United States Patent [19]

Nestor et al.

[11] Patent Number: 4,545,081
[45] Date of Patent: Oct. 8, 1985

[54] SEMI-RIGID PENILE PROSTHESIS WITH SEPARABLE MEMBERS AND POSTURE CONTROL

[76] Inventors: Jack Nestor, 110 1st Terr., Miami Beach, Fla. 33139; John W. Devine, Jr., 4400 Bay Point Rd., Miami, Fla. 33137

[21] Appl. No.: 588,285

[22] Filed: Mar. 12, 1984

Related U.S. Application Data

[63] Continuation of Ser. No. 278,480, Jun. 29, 1981, abandoned.

[51] Int. Cl.⁴ ............................................. A61F 1/00
[52] U.S. Cl. ...................................... 623/11; 128/79; 623/12
[58] Field of Search ................................ 3/1; 128/79

[56] References Cited

U.S. PATENT DOCUMENTS

| | | | |
|---|---|---|---|
| 3,625,200 | 12/1971 | Muller | 128/348 |
| 3,794,041 | 2/1974 | Frei et al. | 128/348 |
| 4,151,840 | 5/1979 | Barrington | 128/79 |
| 4,285,070 | 8/1981 | Averill | 128/92 C |
| 4,411,261 | 10/1983 | Finney | 128/79 |

*Primary Examiner*—Richard J. Apley
*Assistant Examiner*—David Isabella
*Attorney, Agent, or Firm*—Erwin M. Barnett

[57] ABSTRACT

A penile prosthesis has a minor length proximal end member separable from the major length body member enabling insertion separately into the crus and the corpus cavernosum, respectively. An element of a quick engageable connector is formed on the adjacent ends of each member for joining the members together as a unit after each member is properly positioned in the patient. Several connectors are shown. Penile posture control is achieved in the major length body member by an axially extending multiple jointed spine within a silicone rubber casing. The spine is formed with alternate tubular and spherical links retained in an articulating assembly by an axial wire. Each spherical link is formed with a pair of diametric extensions projecting into the bores of adjacent tubular links and a diametric bore through the extensions through which the wire passes. The extensions serve to limit the articulation between adjacent links. A compression spring is incorporated in the spine and, in a modification, a threaded adjustment to be performed during manufacture varies the compressive force between the links exerted by the spring and facilitates providing a selection of body members of different stiffnesses. A region of maximum flexibility for positioning at the base of the penis is provided in the spine by the coaction of the spring with specialized proximal terminal links. A modification provides the region of maximum flexibility at the base of the penis in the structure of the minor length member.

19 Claims, 10 Drawing Figures

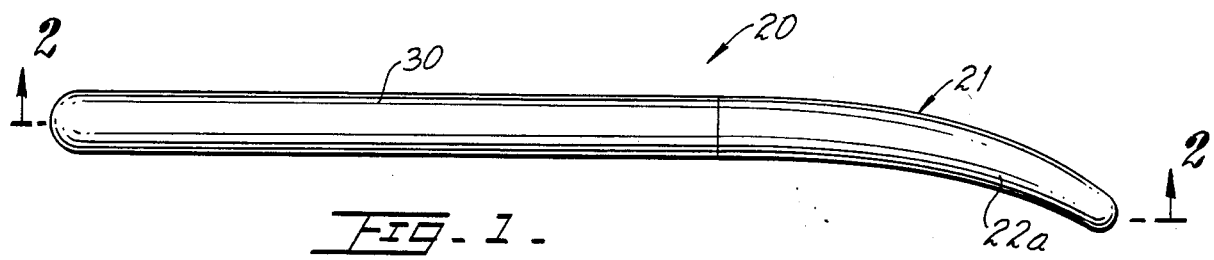
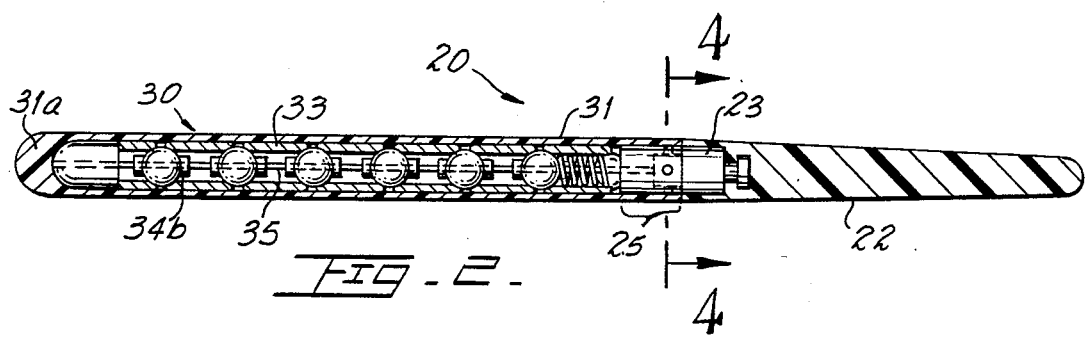
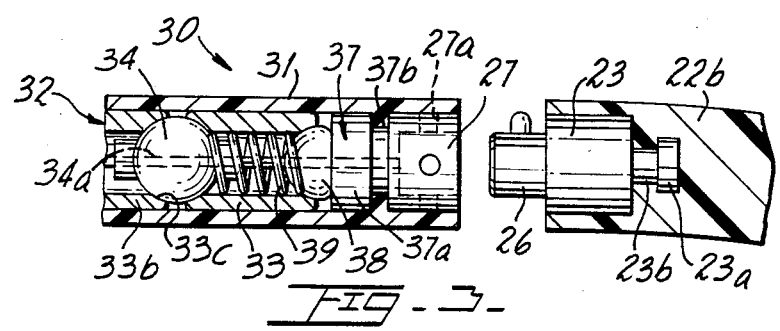
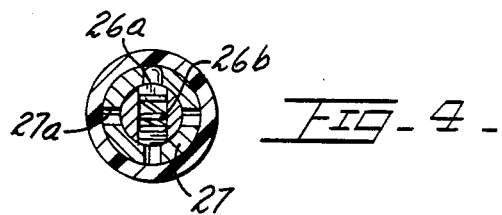

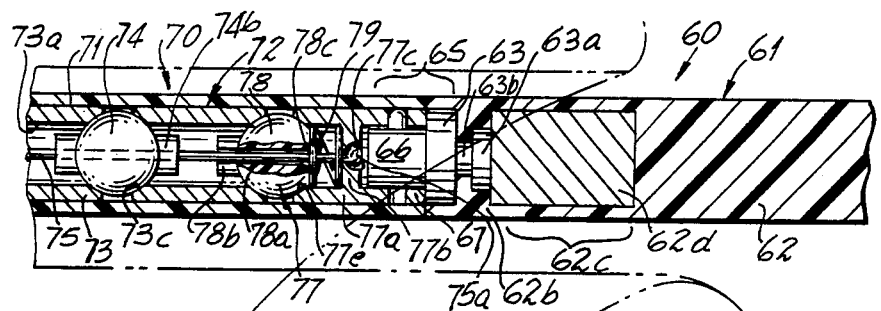
_FIG_-_9_-
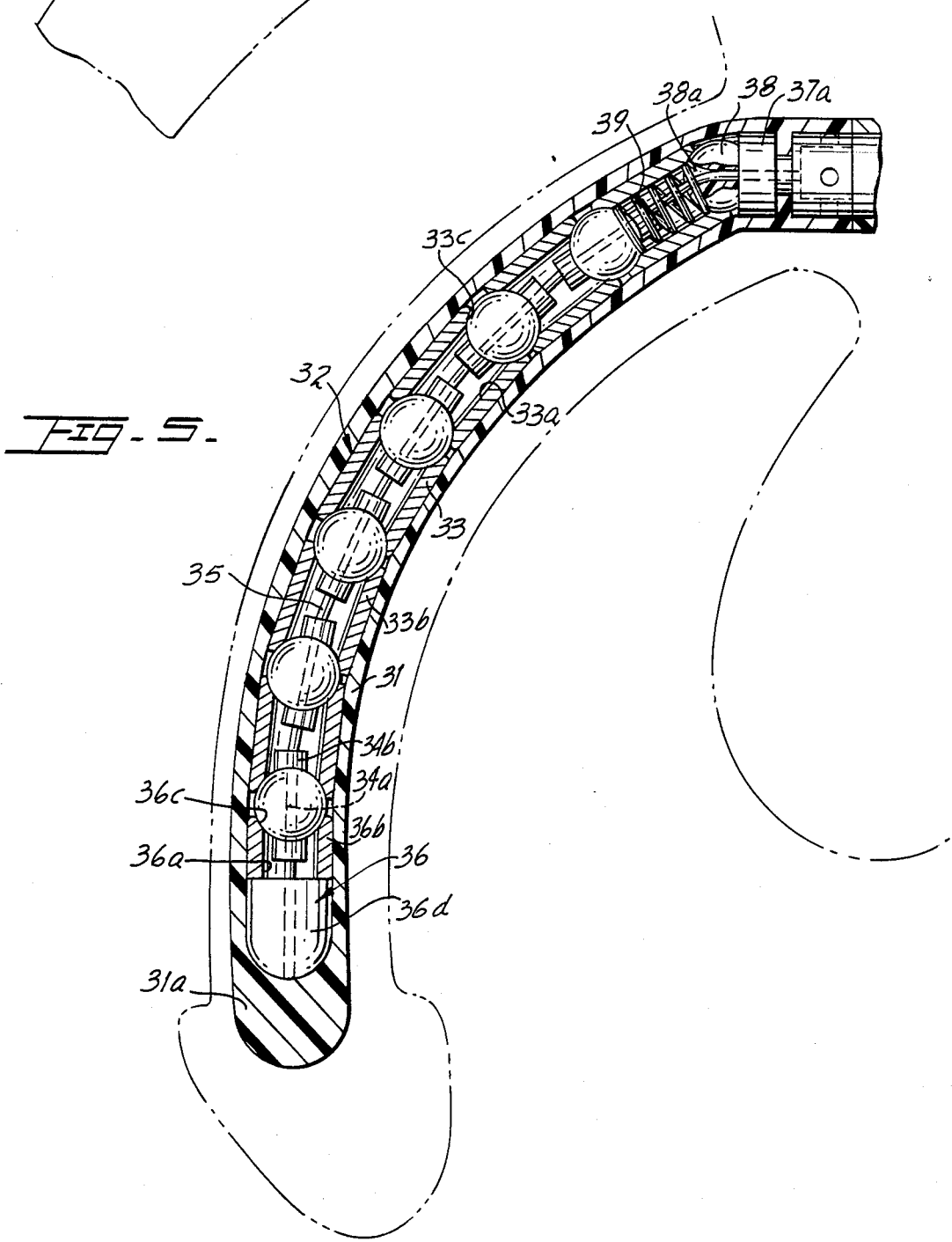
_FIG_-_5_-

SEMI-RIGID PENILE PROSTHESIS WITH SEPARABLE MEMBERS AND POSTURE CONTROL

This is a continuation of Ser. No. 278,480, filed June 29, 1981 abandoned.

BACKGROUND OF THE INVENTION

1. Field of the Invention

This invention relates generally to penile prostheses and more particularly is directed to a prosthesis construction of the semi-rigid type, that is, the type in which the length and diameter are predetermined and fixed, and the proper functioning thereof relies on the ability of the prosthesis when implanted in the corpus cavernosum to change configuration by manipulation of the penis between curved depending positions during micturition and when at rest and an extended straight-line erected position during coitus.

2. Description of the Prior Art

Although the inflatable prosthesis more closely parallels natural function, the semi-rigid prosthesis has remained a viable alternative thereto because of the simplicity of the surgical procedure for implanting the semi-rigid device, the lower cost factor for both surgery and prosthesis, the absence of hydraulic operating parts and the minimal theoretical as well as experienced failure of the implant requiring corrective surgical measures. Recognizing the disadvantages inherent in all semi-rigid prostheses, namely, the inability to change length, diameter and flexural stiffness after implantation, various prior art devices have been suggested, manufactured and implanted in a large number of patients, each form of device having features directed to minimize the practical effects of such inherent characteristics.

Several of these semi-rigid prostheses are designed to assume the straight-line erected state but with varying degrees of flexibility as, for example, the Small-Carrion prosthesis disclosed in U.S. Pat. No. 3,893,456, granted July 8, 1975. This construction requires special underwear or other means to retain the penis out of its erected position in daily living. Finney et al. U.S. Pat. No. 4,066,073, granted Jan. 3, 1978, utilizes a rod having axially arrayed sections of various flexural properties. A proximal section suitable for positioning adjacent the pubis is medium stiff in flexure. A longer distal portion, positioned in the corpus cavernosum, is stiffer than the proximal section and a very flexible hinge portion separates the two. The stiff proximal and distal portions are intended to provide desired stiffness to the penis while the hinge portion is intended to permit the penis to be conveniently and easily bent at its base. The intended improvement by Finney et al over Small-Carrion may be offset by problems with thrust during coitus due to the softness of the hinge. Timm et al. U.S. Pat. No. 3,987,789, granted Oct. 26, 1976, provides the plastic body of the prosthesis with a malleable rod portion enabling the implanted penis to be bent and twisted into a variety of shapes which will be retained until reshaped by further bending. The disclosure calls for a rod of nickel-titanium alloy either solid or of stranded filaments. The rod proved unsatisfactory by breaking after repeated bending. This problem was corrected by utilizing a stranded wire made of nearly pure silver, the use of which is reported by Udo Jonas and Gunther H Jacobi in the Journal of Urology, Vol. 123, June 1980, pages 865-14 867. This silicone-silver prosthesis, although reported in the Jonas et al article as having the characteristic of not fatiguing, breaking or hardening under continuous bending, nevertheless, is capable of bending or twisting into undesirable shapes. Having no resiliency whatsoever, once bent, the penis with this implant remains in such undesirable shape, perhaps resembling a corkscrew, until manually reshaped. This can conceivably occur during coitus.

One of the difficulties encountered in both the perineal and dorsal surgical approaches is the size determination and the insertion of the elongated prosthesis into the entire length of the corpus cavernosum through the longitudinal incision along a midportion thereof. This can now only be accomplished by painstaking and time consuming manipulation and bending of a midportion of the prosthesis at an acute angle in order to insert one end into the crus and the other end into the corpus of the pendulus penis to the base of the glans, not necessarily in that order.

It is therefore apparent that to further minimize the inherent disadvantages of the semi-rigid prosthesis by eliminating the hereinbefore mentioned problems and drawbacks of prior art devices as well as to provide prosthesis constructions requiring smaller incisions and facilitating sizing and insertion will satisfy a present need in the management of male impotency where the use of an implant is indicated.

SUMMARY OF THE INVENTION

Among the objects of the invention is to provide penile prosthesis constructions of the semi-rigid type which will satisfy the needs of the patient in providing comfortable, effective, reliable, maintenance free and foolproof management of impotency and also satisfy the needs of the surgeon in simplifying the procedure, requiring smaller incisions and facilitating size determination and actual implantation.

The prosthesis features a two-piece construction comprising a proximal end member for separately sizing and positioning in the crus of the corpus cavernosum and a body member for separately sizing and positioning in the corpus cavernosum extending through the pendulus penis. The adjacent end portions of each member is formed with an element of a snap-in connector for joining the members, after positioning, into a structural and functional unit. Flexing means is incorporated in the prosthesis enabling the penis to flex at its base between erected and flaccid postures.

Whereas the penis implanted with a prosthesis of the semi-rigid type embodying the invention cannot assume a state equivalent to that defined as flaccid in the normally functioning penis, the term flaccid positure as used in the description herein and in the claims will be understood to designate the postures of the penis in other than the erected state, such as, during micturition and when at rest in a dependent posture.

Another feature of the invention is the non-resiliency of the body member of the prosthesis enabling the latter to retain its posture until a predetermined force is manually applied to the penis to change that posture. This non-resiliency is combined with controlled maximum flexing at the base of the penis and limited flexing along the remaining length thereof. These characteristics are provided by a spine construction comprising an axial wire anchored in proximal and distal end links retaining therebetween a series of tubular links separated by spherical links in ball and socket engagement. The spherical links provide universal movement between adjacent tubular links which movement is constrained by an extended diametric bore structure on each spherical link through which the axial wire extends. The diametric bore structure extensions are housed within the tubular links and each extension cooperates with that of the adjacent spherical link to provide therebetween discrete flexural regions uniformly spaced along the length of the axial wire. The flexing along the length of the body member is limited by contact between the ends of adjacent tubular links as well as by engagement of the bore structure extensions with the walls of the tubular links. The absence of the constraints provides greater flexure at the proximal end of the spine which when implanted satisfies the flexure requirement between erected and flaccid postures. A compression spring, housed in a tubular link, provides friction at the ball and socket joints and hence the resistance of the prosthesis to postural change. Slight differences in resistance may be achieved in the manufacture of the body member by an adjustment incorporated in the spine to vary the effective length of the axial wire and hence the force exerted by the compression spring.

BRIEF DESCRIPTION OF THE DRAWINGS

FIG. 1 is a top plan view of the two-piece penile prosthesis constructed to embody the invention shown assembled and in the extended configuration for providing an erected posture of the penis.

FIG. 2 is a sectional view taken on line 2—2 in FIG. 1 showing interior construction.

FIG. 3 is an enlarged fragmentary sectional view of the region of the connector taken similar to FIG. 2 but showing the members separated.

FIG. 4 is an enlarged sectional view taken on line 4—4 in FIG. 2 showing details of the connector.

FIG. 5 is an enlarged fragmentary sectional view of the body member of the prosthesis shown in FIG. 2 but in a flexed and curved configuration of the flaccid posture of the penis, an outline of the genital region being indicated in phantom depicting implantation.

FIG. 9 is an enlarged fragmentary sectional view of another modified prosthesis wherein the connector is distal to the region of flexure at the base of the penis, an outline of the penis being shown in phantom with respect to the prosthesis shown in full lines in erected posture, the flaccid posture of the penis also being indicated in phantom.

DESCRIPTION OF THE PREFERRED EMBODIMENTS

Figure 6:
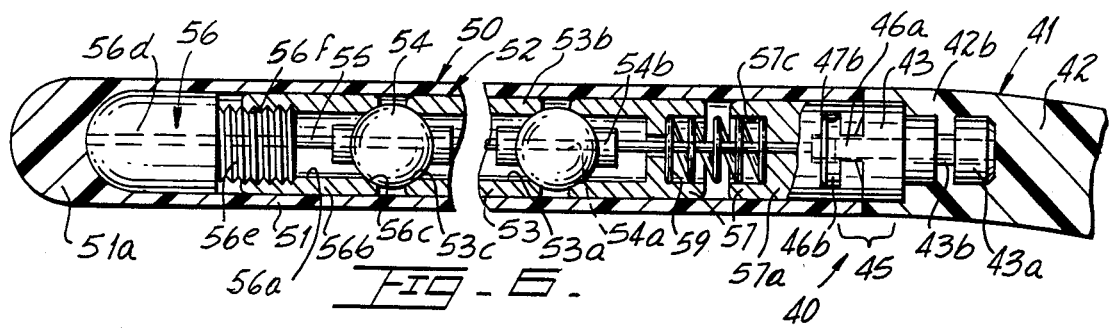
FIG. 6 is an enlarged fragmentary sectional view of a prosthesis embodying the invention having a modified spine construction and an alternative type of connector and shown in an erected posture.

Referring in detail to the drawings, 20 generally denotes a penile prosthesis embodying the invention shown in FIGS. 1 to 5, inclusive, as a two-piece structure comprising a proximal end member 21 of minor length separably connected to a body member 30 of major length. Proximal end member 21 is seen in FIG. 1 to comprise portion 22 having a free end section 22a tapered and curved laterally to conform to the crus of the corpus cavernosum and an anterior end 22b having embedded therein plug 23 which terminates in one element 26 of a quick engageable snap in connector 25. Portion 22 is made of a suitable physiologically inert medical grade elastomer, such as silicone rubber, which can be manufactured to desired specifications of hardness and flexibility.

Body member 30 is seen in FIGS. 2 and 5 to comprise a spine 32 having a plurality of segments joined together for controlled ball and socket relative universal movement encased in a sheath 31 made of a material similar to portion 22. Spine 32 comprises a plurality of tubular links 33 alternating with a plurality of spherical links 34, each of the latter being formed with a pair of diametrically located bosses or extensions 34b and a diametric bore 34a aligned with and extending axially through bosses 34b. Each tubular link 33 may be cylindrical in shape and is shown to be slightly larger in diameter than spherical links 34 and has a relatively large bore 33a into which bosses 34b of the adjacent spherical links 34 project at opposite ends 33b. Each end 33b is formed with a curved chamfer 33c seen in FIGS. 3 and 5 to conform to the spherical contour of link 34 providing a socket element of a ball and socket joint between spherical link 34 and the adjoining tubular links 33. An axial wire 35, suitably anchored in the axial bores of terminal links 36 and 37 located at opposite ends of spine 32, extends through bores 33a and 34a and retains all links 33 and 34 therebetween in operative engagement.

Distal terminal link 36 has an inner end portion 36b formed with bore 36a and a curved chamfer 36c, the latter seating adjacent spherical link 34 thereagainst with boss 34b extending into bore 36a. The free end 36d of link 36 has a rounded contour which is covered by a paraboloidal cushioning tip 31a of sheath 31, end 36d also providing means for suitably anchoring axial wire 35 therein as by swaging in a reduced diameter bore. Proximal terminal link 37 is seen in FIGS. 2, 3 and 5 to comprise a cylindrical body 37a in which said wire 35 is suitably anchored and a link engaging end 38 formed in a spherical contour of a diameter equal to that of spherical links 33. Link engaging end 38, as seen in FIG. 5, is formed with an inwardly tapered or conical bore 38a giving axial wire 35 freedom of movement therein. The opposite end of body 37a is formed as an element 27 of connector 25. The exterior surface of cylindrical body 37a may be suitably roughened to prevent relative movement between sheath 31 and terminal link 37, as for example, by a plurality of surface recesses or, as shown, by an annular groove 37b in which a complementary portion of sheath 31 engages. A helical compression spring 39 through which wire 35 extends is housed in bore 33a of the tubular link 33 adjacent terminal link 37 and engages spherical end 38 and spherical link 34 at opposite ends thereof exerting a separating force therebetween.

Connector 25 is of a type wherein the separate male and female elements are brought into engagement by relative axial movement and, as illustrated in FIGS. 3 and 4, comprises male element 26 axially extending from plug 23 and sized to telescopingly fit female element 27 integrally formed as an enlarged bore in the free end of cylindrical body 37a. Suitable snap-in retaining means between elements 26 and 27 are seen in FIG. 4 to include openings 27a arranged in 90° relation for selectively engaging T-shaped pin 26a which is housed in male element 26 and biased into an extended position by a compression spring 26b. The embedded end of plug 23 may be formed with an axial knob 23a providing an undercut groove 23b into which complementary material of portion 22 extends retaining plug 23 against separation from portion 22.

Plug 23 and tubular links 33, terminal links 36 and 37, axial wire 35 and compression spring 39 of spine 32 may all be made of corrosion resistant metal, such as, stainless steel or a titanium alloy for lighter weight. Spherical links 34 are illustrated as being made of a plastic, such as, rigid nylon or teflon, but may also be made of metal while tubular links 33 may be plastic.

The practical utility and operation of prosthesis 20 will now be apparent. Proximal end members 21 and body members 30 are supplied individually in a range of different sizes. Proximal end members 21 are readily molded to desired size differences. Larger differences in the lengths of body members 30 may be provided by varying the number of tubular links 33 and spherical links 34 in spine 32, while smaller size differences are provided by varying the effective lengths of cushioning tip 31a and rounded end 36d of link 36.

Implantation of prosthesis 20 is performed utilizing either the perineal or dorsal approach to provide a longitudinal incision in a midportion of one of the corpora cavernosa. The corpus is dilated proximally and distally to the full length thereof in accordance with established surgical procedure and anatomical measurements taken. A proximal end member 21 of appropriate size is inserted and fitted to occupy the length of the crus. The length for body member 30 may be determined by extending the penis to its full length and taking the measurement externally. The respective lengths of members 21 and 30 are selected to insure that the region of maximum flexibility of member 30, namely, the joint between spherical end 38 of proximal terminal link 37 and the adjacent tubular link 33, is located at the base of the penis where the maximum flexure is required, as seen in FIG. 5. After the two members 21 and 30 are inserted and fit properly, connector element 26 is snapped into engagement with element 27, there being sufficient give in the tissue to permit axial alignment of the separate elements 26 and 27 prior to making the connection. A similar procedure is followed to implant a prosthesis 20 in the other corpus cavernosum.

It is thus apparent that a patient's penis having prostheses 20 implanted in the corpora will have the capability of being easily manipulated from an erected posture for coitus to a variety of flaccid postures including a downwardly inclined posture for micturition, a gently curved depending posture shown in FIG. 5 or a curved posture slightly more extreme than FIG. 5 wherein the distal end rests more closely to the patient's body. A predetermined manual force is required to change posture and the extent of flexure is controlled within predetermined limits. The amount of force and the extent of flexure are both determined by the structure of spine 32.

The uniformly spaced joints between tubular links 33 at each spherical link 34 along spine 32 eliminates the possibility of sharp bends in body member 30. Furthermore, additional bending between adjacent tubular links 33 from the gentle curved posture shown in FIG. 5 will ultimately result in contact between boss 34b of each spherical link 34 and the wall of bore 33a of the tubular link 33 in which boss 34b is contained and also in contact between ends 33b of adjacent links 33. These contacts limit bending between the adjacent links 33 to a maximum of 15° to 20° and predetermine a minimum radius of curvature for spine 32. The region of maximum flexibility of member 30 provided at the joint between proximal terminal link 37 and the adjacent tubular link 33 is achieved by the spherical end 38 and tapered bore 38a which communicates directly with bore 33a of adjacent link 33. This action increases the bending limit of the joint to between 35° and 45°.

All changes of posture of the penis is a result of movement at the joints along spine 32 and bending of axial wire 35 in the region between bosses 34b of adjacent spherical links 34 and between spherical end 38 and adjacent spherical link 34. The resistance to such movement, therefore, depends upon the force required to overcome any stiffness in axial wire 35, which has non-resilient properties, and the friction within the joints. It is thus clear from FIG. 5 that resistance to bending in the region of maximum flexibility, in addition to any stiffness in axial wire 35, is provided by the friction between spherical end 38 and compression spring 39, the force being supplied by spring 39. Likewise, resistance to posture change along the length of the pendulus penis is provided by friction within the joints along spine 32 in addition to stiffness in axial wire 35. This friction is also provided by spring 39 which, by contacting adjacent spherical link 34, exerts a force thereagainst for friction therewith, the force and the friction created thereby being transmitted to all the other joints along spine 32. Bores 34a are diametrically sized to snugly fit axial wire 35 yet permit spherical links 34 to slide therealong. Axial wire 35, which may be solid but preferably is of multi-stranded stock, has an effective length to load spring 39 to a predetermined degree and permit a loose fit of the tubular link 33 adjacent spherical end 38, which link serves primarily as a housing for the interior structure. Compression spring 39, in applying a tension to axial wire 35, aids smooth bending and the elimination of kinking in axial wire 35.

Figure 7:
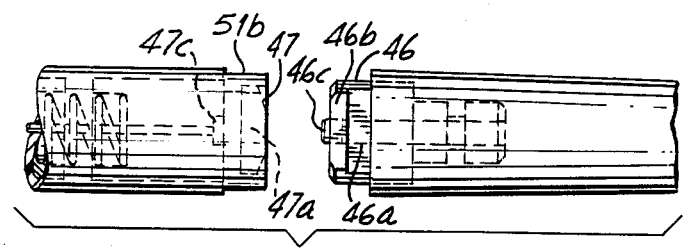
FIG. 7 is an elevational view of the region of the connector in FIG. 6 but showing the members separated.
Figure 8:
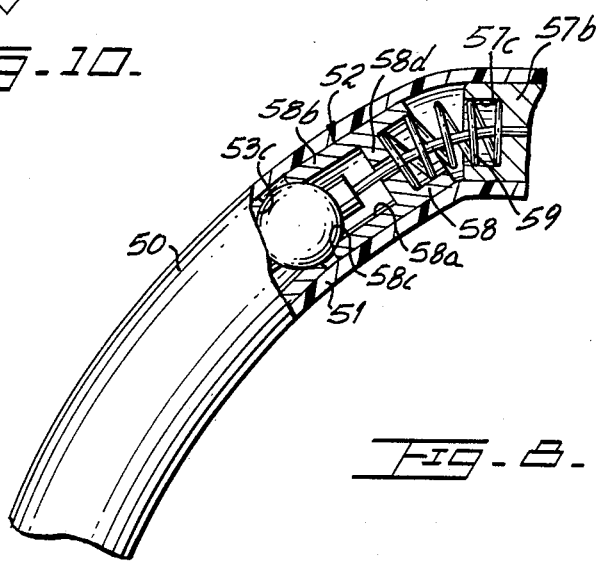
FIG. 8 is a fragmentary side elevational view partly in section of the body member of the prosthesis in FIG. 6 shown flexed to a flaccid posture.

A modified embodiment of the invention is illustrated in FIGS. 6, 7 and 8 as a two-piece prosthesis 40 comprising proximal end member 41 separably connected to body member 50. Proximal end member 41 comprises portion 42 having a tapered and laterally curved free end section similar to section 22a of proximal end member 21 and an anterior end 42b having embedded therein plug 43 which terminates in one element 46 of quick engageable connector 45.

Body member 50 has a spine 52 encased in sheath 51 and comprising tubular links 53, spherical links 54 and an axial wire 55 anchored at opposite ends in terminal links 56 and 57. Tubular links 53 are similar to links 33, having large bores 53a, and opposite ends 53b formed with curved chamfers 53c. Likewise, spherical links 54 are similar to spherical links 34, having pairrs of diametric bosses 54b and diametric bores 54a extending therethrough.

Distal terminal link 56 is a threadedly connected two-piece structure comprising a rounded tip and anchor section 56d having male threads 56e engaging female threads 56f formed in one end of bore 56a of a tubular section 56b, the opposite end of which has a curved chamfer 56c for seating adjacent spherical link 54 thereagainst. Proximal link 57 is also a two-piece structure comprising an anchor and connectorsection 57a and a modified tubular link section 58 with a helical compression spring 59 interposed therebetween. Section 57a comprises a cylindrical body 57b in which axial wire 55 is suitably anchored and having an inner end formed with a bore 57c in which one end of spring 59 seats. The opposite end of section 57a is formed as an element 47 of connector 45. Tubular link section 58 has an axial bore 58a and is formed at anterior end 58b with a curved chamfer 58c engaging adjacent spherical link 54. An interior flange 58d extending into a midportion of bore 58a provides a shoulder against which the other end of spring 59 abuts.

Connector 45 is of a type wherein separate male and female elements are engaged by movement perpendicular to the longitudinal axes of members 41 and 50 after the elements are aligned in a laterally offset position. Thus, plug 43 has a male element 46 formed in a T-shaped configuration providing a diametrically extending post 46a from which a pair of tongues 46b laterally extend. Female element 47 is formed in the free end of cylindrical body 57b as a diametric slot 47a opening into a pair of laterally extending grooves 47b. Suitagle snap-in retaining means includes an axial depression 47c and a spring biased button 46c projecting from post 46a for snapping into engagement with depression 47c when the elements are in axial alignment. Sheath 51 has a thickened tip 51a fir cushioning distal terminal link 56 and also has cutouts 51b at opposite ends of diametric slots 47a and grooves 47b for access thereto by post 46a and tongues 46b, respectively.

Members 41 and 50 of prosthesis 40 are separately inserted into the corpus cavernosum in the manner described for prosthesis 20. To effect engagement of connector 45, male element 46 is brought into an overlapping, laterally offset position with respect to female element 47 with post 46a and tongues 46b aligned with slot 47a and grooves 47b, respectively. Lateral movement of element 46 with respect to element 47 will bring the parts into engagement in axial alignment so that button 46c engages in depression 47c.

The action of spring 59 is similar to that of spring 39 with respect to providing the friction in the joints between tubular links 53 along the length of member 50. The operation of body member 50 in the region of maximum flexibility differs from that of body member 30, relying on the bending of both axial wire 55 and helical spring 59 so that the resistance to change of posture depends on the stiffness of axial wire 55. The threaded connection in the distal link 56 between tip and anchor section 56d and tubular section 56b provides an adjustment in the effective length of axial wire 55 and hence in the separation between anchor and connector section 57a and tubular section 58 of proximal link 57 and to the loading of compression spring 59. This adjustment is made during manufacture and facilitates production of body members 50 in a selection of different stiffnesses.

Another modified embodiment of the invention is illustrated in FIG. 9 as a two-piece prosthesis 60 in which the relative lengths of proximal end member 61 and body member 70 serve to locate separable connector 65, when prosthesis 60 is implanted, distally with respect to the base of the penis so that structural means enabling flexure of the penis at its base between erected and flaccid postures is incorporated in proximal end member 61 adjacent plug 63 rather than in the proximal terminal link 77 of body member 70 as are terminal links 37 and 57 of body members 30 and 50, respectively, Accordingly, proximal end member 61 has an overall length proportionally greater with respect to body member 70 than end members 21 and 41 of prostheses 20 and 40, respectively, and incorporates therein a region 62c of flexible bending just proximally of connector 65. The free end section (not shown) of proximal end member 61 is tapered and curved similar to free end section 22a of member 21 and the end of anterior section 62b similarly mounts plug 63 from which the male element 66 of connector 65 extends. Immediately adjacent plug 63 anterior section 62b is elongated to accommodate flexible region 62c which may be made as a core 62d of suitable soft, low density elastomeric material.

Body member 70 along most of its length may be similar to body members 30 or 50 having a rubber sheat 71 encasing spine 72 which comprises a plurality of tubular links 73 alternating with spherical links 74 and an axial wire 75 extending therethrough and anchored at opposite ends in a distal link (not shown) and proximal terminal link 77. The distal terminal link may be similar to link 36 of spine 30 or may incorporate tension adjustability in the manner of two-piece link 56 of spine 52. Proximal link 77 may be a two-piece structure comprising an anchor and connector section 77a and a modified spherical link 78 with a helical compression spring 79 acting therebetween. Female element 67 of connector 65 is formed as an enlarged bore in the free end of section 77a and has snap-in retaining means similar to openings 27a in element 27. The midportion of section 77a provides suitable means for anchoring the proximal end of axial wire 75 shown as a transverse wall 77b, wire 75 extending through a small axial opening therein and terminating in a enlargement, such as knot 75a, which is seated in a depression 77c providing clearance from male element 66. Transverse wall 77b separates the bore of female element 67 from the bore which houses spring 79 and terminates in a curved chamfer 77e providing a socket for spherical link 78. The latter is a modified form of spherical link 74, having a single boss 78b extending into the axial bore 73a of the adjacent tubular link 73. Diametric bore 78a extends through boss 78b and has a conical enlargement 78c opening into bore 77d to provide desired flexibility thereat.

Members 61 and 70 of prosthesis 60 are separately inserted into the corpus cavernosum in the manner described for prosthesis 20 but require positioning region 62c at the base of the penis in the region of maximum flexibility with connector 65 appropriately located distally thereof. The multiple joint construction with coacting spring 79 of spine 72 provide the same flexibility for gentle curvature to the pendulus penis and resistence to change of posture as spines 32 and 52. A selection of proximal end members 61 having flexible regions 62c of different lengths may be provided to satisfy anatomical differences in patients. A suitable axial wire (not shown) having desired properties of non-resiliency and stiffness may be attached at one end to plug 63 and extend posteriorly through core 62d into the denser silicone rubber portion 62 to improve the resistance to change of posture characteristics of flexible region 62c.

Figure 10:
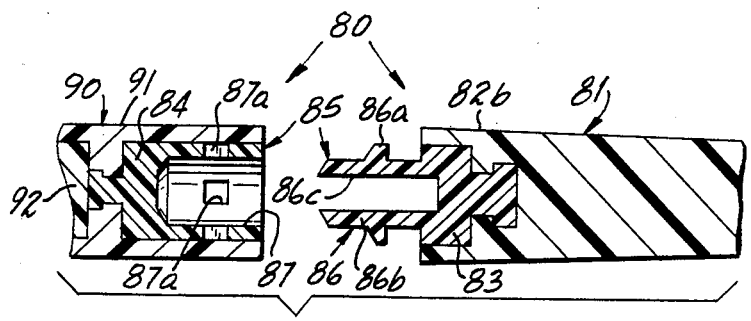
FIG. 10 is a fragmentary sectional view of the region of the connector of another prosthesis showing a modified connector incorporated therein with the members separated.

A separable connector is shown in FIG. 10 as part of modified two-piece prosthesis 80 which comprises proximal end member 81 and body member 90. End member 81 is similar to members 21 and 41, the anterior end 82b having a plug 83 embedded therein. Body member 90 is intended to include any of various known types of flexure core constructions generally designated 92 and encased in a sheath 91 and fitted with a terminal plug 84 in a manner similar to plug 83. While metal may be used, both plugs 83 and 84 are illustrated as made of plastic material which will have suitable physiologically inert properties, plug 83 also having a resiliency for its intended snap-in function.

Separable connector 85 comprises a male element 86 integrally formed with plug 83 sized and shaped to fit the bore of female element 87 formed in plug 84. A diametric cutout 86c divides element 86 into two resilient prongs 86b having diametric projections 86a as an element of a snap-in retaining means which engage diametric openings 87a in female element 87 when the connection is made. The beveled leading edges of projections 86a enable prongs 86b to flex toward each other in the well understood manner when male element 86 is inserted into female element 87. Two pairs of diametric openings 87a are shown in right angular relation to facilitate alignment of members 81 and 90. Whereas, the characteristics of the particular flexure core construction 92 determines the functioning of the implanted prosthesis 80, connector 85 provides the advantages of a separable two-piece unit during surgery and implantation.

Although not always apparent in the drawings, the respective edges of female elements 27, 47 and 87 are suitably rounded or beveled in order to facilitate the depression of pin 26a and button 46c, and the flexing of prongs 86b of male elements 26, 46 and 86, respectively, when the connection is being made. It is also intended that, once assembled, these retaining means will resist ordinary forces attempting separation. However, in the event it becomes necessary to remove the prostheses after the connection is made, disengagement may be accomplished by piercing or otherwise removing the sheath in the region of openings 27a or 87a rendering pin 26a and projections 86a accessible for depression by a suitable tool. In connector 45, a transverse bore (not shown) is intended to be formed in anchor and connector section 57a to extend from the exterior into axial depression 47c providing accessibility for the release of button 46c by a suitable tool.

Within the scope of the invention, equivalent components in prostheses 20, 40, 60 and 80 may be interchanged with each other. For example, prosthesis 20 may be provided with connector 45 and/or the adjustable two-piece distal terminal link 56 shown in prosthesis 40, or the latter may be provided with connector 25. Likewise, the male and female elements of the connectors may be reversed. Also, a single prosthesis implanted in one side of the penis may render acceptable results.

The penile prostheses herein disclosed are seen to achieve several objects of the invention and to be well adapted to meet conditions of practical use. As various possible embodiments might be made of this invention, and as various changes might be made in the disclosed prostheses, it is to be understood that all matter herein set forth or shown in the accompanying drawings are to be interpreted as illustrative and not in a limiting sense.

What is claimed is:

1. A penile prosthesis of the sem-rigid type comprising a proximal end member for separately sizing and implanting in the crus of the corpus cavernosum and a body member of predetermined semirigidity for separately sizing and implanting in the corpus cavernosum within the pendulus penis, each of said members having an adjacent end portion formed with an element of a quick engageable snap-in connector whereby said members are joined into a structural and functional unit after said separate sizing and implanting of the members, said unit having flexure means located in the region of the base of the penis when said members are implanted and joined permitting movement of the penis between erected and flaccid positions.

2. The penile prosthesis defined in claim 1 in which said flexure means is located in said body adjacent said connector element thereof.

3. The penile prosthesis defined in claim 1 in which said flexure means is located in said proximal end member adjacent said connector thereof.

4. The penile prosthesis defined in claim 1 in which said elements of the snap-in connector include means for joining the elements by axial alignment and movement toward each other into snap-in engagement.

5. The penile prosthesis defined in claim 1 in which said elements of the snap-in connector include means for joining the elements by movement perpendicular to the longitudinal axis of said members from an offset, overlapping lateral alignment of the elements into snap-in axial alignment thereof.

6. The penile prosthesis defined in claim 2 in which said flexure means has a predetermined resistance to bending requiring application of manual force for movement thereat.

7. A penile prosthesis having a body member sized to extend through the corpus cavernosum within the pendulus penis and a proximal end member sized to extend through the crus and said body member and said proximal end member are separate structures for inserting individually into the corpus and crus wherein each member includes an element of a quick engageable snap-in connector for joining said members into a structural and functional unit after said individual insertion, a spine encased in said body member, said spine having a non-resilient, stiffening longitudinal portion of predetermined flexibility extending substantially the length thereof and terminating in an end portion of greater flexibility with respect to said predetermined flexibility, when implanted said body and proximal end members cooperating to position said spine end portion at the base of the penis, said spine longitudinal portion enabling said body member to be manually flexed along a predetermined length thereof between an extended straight-line configuration for a penile erected posture and gentle curved configurations for flaccid penile postures, said spine longitudinal portion including means for limiting said flexure along said length of the body member to a predetermined curvature.

8. The penile prosthesis defined in claim 7 in which said spine end portion of greater flexibility includes means of a predetermined resistance to bending requiring application of manual force for movement thereat.

9. The penile prosthesis defined in claim 7 in which said spine longitudinal portion comprises an axial wire anchored at opposite ends in proximal and distal end links retaining therebetween a plurality of tubular links separated by spherical links in ball and socket engagement with the tubular links, said ball and socket engagement providing spaced movable joints between adjacent tubular links for said flexibility of the spine longitudinal portion.

10. The penile prosthesis defined in claim 9 in which said spine end portion of greater flexibility is a joint between said proximal end link and an adjacent tubular link.

11. The penile prosthesis defined in claim 10 in which said spine end portion includes means of predetermined resistance to bending, said proximal end link having an inner end terminating in a spherical contour, said means of predetermined resistance to bending including a helical compression spring through which said axial wire extends, said spring exerting a predetermined force against said spherical contour.

12. The penile prosthesis defined in claim 9 in which said spine end portion is located in said proximal end link, the latter being a two-piece structure having interposed therebetween a helical compression spring through which said axial wire extends.

13. The penile prosthesis claimed in claim 9 in which each of said spherical links has a pair of diametrically oppositely extending bosses through which an extended diametric bore passes, said axial wire extending through said extended diametric bore, said bosses extending into the bores of adjacent tubular links and being spaced from the bosses of adjacent spherical links providing therebetween discrete flexural regions along said axial wire, said bosses being components of said spine longitudinal portion flexure limiting means.

14. The penile prosthesis defined in claim 13 in which said spine longitudinal portion includes means of predetermined resistance to flexing along the body member length requiring application of manual force for altering the configuration thereof, said means of predetermined resistance including a helical compression spring housed in one of said tubular links exerting a predetermined compressive force against said spaced joints providing a component of said predetermined resistance.

15. The penile prosthesis defined in claim 13 in which said bosses are proportioned to engage the interior surfaces of the wall of said adjacent tubular links to prevent excessive bending at each of said spaced joints, said engagement serving as said limiting means for said flexure along said length of the body member.

16. The penile prosthesis defined in claim 9 in which said spine longitudinal portion includes means of predetermined resistance to flexing along said body member length requiring application of manual force for altering the configuration thereof, said spine end portion including means of predetermined resistance to bending, a helical compression spring coaxially mounted on said axial wire exerting a compressive force on said spaced joints, said helical spring being a component of said means of predetermined resistance to flexing and said means of predetermined resistance to bending.

17. The penile prosthesis defined in claim 16 in which said spine includes a link having threaded axial adjustment means for varying the effective length of said wire to adjust the compression of said spring during assembly of the spine.

18. A penile prosthesis having a body member sized to extend through the corpus cavernosum within the pendulus penis and a proximal end member sized to extend through the crus, a spine encased in said body member, said spine having a non-resilient, stiffening longitudinal portion of predetermined flexibility extending substantially the length thereof enabling said body member to be manually flexed along a predetermined length thereof between an extended straight-line configuration for a penile erected posture and gentle curved configurations for flaccid penile postures, said spine longitudinal portion comprising an axial wire anchored at opposite ends in proximal and distal end links retaining therebetween a plurality of tubular links separated by spherical links in ball and socket engagement with the tubular links, said ball and socket engagement providing spaced movable joints between adjacent tubular links for said flexibility of the spine longitudinal portion, each spherical link having a pair of diametrically oppositely extending bosses through which an extended diametric bore passes, said axial wire extending through said extended diametric bores, said bosses extending into the bores of adjacent tubular links and being spaced from the bosses of adjacent spherical links providing therebetween discrete flexural regions along said axial wire.

19. The penile prosthesis defined in claim 18 in which said bosses are proportioned to engage the interior surfaces of the wall of said adjacent tubular links to prevent excessive bending at each of said spaced joints, said engagement serving to limit the extend of said body member flexibiliy.

* * * * *